US009382180B2

(12) United States Patent
Miller et al.

(10) Patent No.: US 9,382,180 B2
(45) Date of Patent: Jul. 5, 2016

(54) HYDROFORMYLATION PROCESS

(71) Applicant: Dow Technology Investments LLC, Midland, MI (US)

(72) Inventors: Glenn A. Miller, South Charleston, WV (US); Thomas C. Eisenschmid, South Charleston, WV (US); Rick B. Watson, Freeport, TX (US); Michael A. Brammer, Freeport, TX (US); Michael C. Becker, Texas City, TX (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/648,468

(22) PCT Filed: Nov. 21, 2013

(86) PCT No.: PCT/US2013/071126
§ 371 (c)(1),
(2) Date: May 29, 2015

(87) PCT Pub. No.: WO2014/088816
PCT Pub. Date: Jun. 12, 2014

(65) Prior Publication Data
US 2015/0307430 A1    Oct. 29, 2015

Related U.S. Application Data

(60) Provisional application No. 61/734,089, filed on Dec. 6, 2012.

(51) Int. Cl.
*C07C 45/50* (2006.01)
*B01J 31/18* (2006.01)

(52) U.S. Cl.
CPC .............. *C07C 45/50* (2013.01); *B01J 31/185* (2013.01); *B01J 2231/321* (2013.01); *B01J 2531/822* (2013.01); *Y02P 20/582* (2015.11)

(58) Field of Classification Search
CPC ..................................................... C07C 45/50
USPC ........................................................ 568/454
See application file for complete search history.

(56) References Cited

U.S. PATENT DOCUMENTS

| | | |
|---|---|---|
| 3,415,906 A | 12/1968 | Shepard et al. |
| 3,527,809 A | 9/1970 | Pruett et al. |
| 4,148,830 A | 4/1979 | Pruett et al. |
| 4,247,486 A | 1/1981 | Brewester et al. |
| 4,329,507 A | 5/1982 | Takeda et al. |
| 4,518,809 A | 5/1985 | Forster et al. |
| 4,528,403 A | 7/1985 | Tano et al. |
| 4,567,302 A | 1/1986 | Sivaramakrishnan |
| 4,567,306 A | 1/1986 | Dennis et al. |
| 4,593,127 A | 6/1986 | Bunning et al. |
| 4,599,206 A | 7/1986 | Billig et al. |
| 4,668,651 A | 5/1987 | Billig et al. |
| 4,717,775 A | 1/1988 | Billig et al. |
| 4,748,261 A | 5/1988 | Billig et al. |
| 4,769,498 A | 9/1988 | Billig et al. |
| 4,774,361 A | 9/1988 | Maher et al. |
| 4,835,299 A | 5/1989 | Maher et al. |
| 4,885,401 A | 12/1989 | Billig et al. |
| 5,059,710 A | 10/1991 | Abatjoglou et al. |
| 5,102,505 A | 4/1992 | Sorensen |
| 5,110,990 A | 5/1992 | Blessing et al. |
| 5,113,022 A | 5/1992 | Abatjoglou et al. |
| 5,179,055 A | 1/1993 | Wink et al. |
| 5,202,297 A | 4/1993 | Lorz et al. |
| 5,235,113 A | 8/1993 | Sato et al. |
| 5,254,741 A | 10/1993 | Lorz et al. |
| 5,264,616 A | 11/1993 | Roeper et al. |
| 5,277,532 A | 1/1994 | Pazzaglia |
| 5,288,918 A | 2/1994 | Maher et al. |
| 5,312,996 A | 5/1994 | Packett |
| 5,360,938 A | 11/1994 | Babin et al. |
| 5,364,950 A | 11/1994 | Babin et al. |
| 5,391,801 A | 2/1995 | Sato et al. |
| 5,430,194 A | 7/1995 | Barner et al. |
| 5,491,266 A | 2/1996 | Babin et al. |
| 5,527,950 A | 6/1996 | Hansen et al. |
| 5,681,473 A | 10/1997 | Miller et al. |
| 5,710,344 A | 1/1998 | Breikss et al. |
| 5,728,893 A | 3/1998 | Becker et al. |
| 5,731,472 A | 3/1998 | Leung et al. |
| 5,741,942 A | 4/1998 | Bryant et al. |
| 5,741,944 A | 4/1998 | Bryant et al. |
| 5,741,945 A | 4/1998 | Bryant et al. |
| 5,744,649 A | 4/1998 | Bryant et al. |
| 5,756,854 A | 5/1998 | Bahrmann et al. |
| 5,763,677 A | 6/1998 | Bryant et al. |

(Continued)

FOREIGN PATENT DOCUMENTS

| | | |
|---|---|---|
| CN | 101722048 | 11/2011 |
| EP | 420510 | 4/1991 |
| WO | 8808835 | 11/1988 |

OTHER PUBLICATIONS

Monteil, et al., "Behaviour of water-soluble dinuclear rhodium complexes in the hydroformylation reaction of oct-1-ene", Journal of Organometallic Chemistry, vol. 480, 1994, pp. 177-184.
Asami, et al., "Production of Oxygen Containing Fuels From Synthesis Gas", Fuel Chemistry Dvision Preprints, vol. 47, No. 2, 2002, pp. 517-518.
Kanagasabapathy, et al., "Hydroformylation with Water- and Methanol-soluble Rhodium Carbonyl/phenyl-sulfonatoalkyl-phosphine Catalyst Systems—A New Concept for the Hydrofoylation of Higher Molecular Olefins", Journal Fuer Praktische Chemie, vol. 337, No. 6, Jan. 1, 1995, pp. 446-450.
Diebolt, et al., "Formation of Acetals under Rhodium-Catalyzed Hydroformylation Conditions in Alcohols", Advanced Synthesis & Catalysis, 354, Issue 4, Mar. 2012, pp. 670-677.
Ali, et al., "Selective hydroformylation—acetalization of aryl alkenes in methanol catalyzed by RhCI3•3H2O—P(OPh)3 system", Journal of Molecular Catalysis A, 2005, 230, p. 9-16.
CRC Handbook of Chemistry and Physics, 72nd Ed., 1991-1992, CRC Press, p. 1-10.

(Continued)

*Primary Examiner* — Sikarl Witherspoon

(57) ABSTRACT

A hydroformylation process that tolerates a high level of methanol in the feed.

12 Claims, No Drawings

(56) References Cited

U.S. PATENT DOCUMENTS

| | | | |
|---|---|---|---|
| 5,914,433 | A | 6/1999 | Marker |
| 5,929,289 | A | 7/1999 | Abatjoglou et al. |
| 5,932,772 | A | 8/1999 | Argyropoulos et al. |
| 5,952,530 | A | 9/1999 | Argyropoulos et al. |
| 6,265,620 | B1 | 7/2001 | Urata et al. |
| 6,307,110 | B1 | 10/2001 | Argyropoulos et al. |
| 6,310,261 | B1 | 10/2001 | Geissler et al. |
| 6,440,891 | B1 | 8/2002 | Maas et al. |
| 7,009,068 | B2 | 3/2006 | Schmutzler et al. |
| 7,145,042 | B2 | 12/2006 | Volland et al. |
| 7,196,230 | B2 | 3/2007 | Peng et al. |
| 7,495,134 | B2 | 2/2009 | Hess et al. |
| 7,582,802 | B2 | 9/2009 | Caers et al. |
| 7,586,010 | B2 | 9/2009 | Liu et al. |
| 7,615,645 | B2 | 11/2009 | Volland et al. |
| 7,655,821 | B1 | 2/2010 | White et al. |
| 7,674,937 | B2 | 3/2010 | Tolleson et al. |
| 7,872,156 | B2 | 1/2011 | Liu et al. |
| 8,003,816 | B2 | 8/2011 | Selent et al. |
| 2005/0209469 | A1 | 9/2005 | Shutt et al. |
| 2010/0006980 | A1 | 1/2010 | Yoshinaga |
| 2010/0267911 | A1 | 10/2010 | Gonzalez et al. |

OTHER PUBLICATIONS

Guo, et al., Hydroformylation of 1-hexene with Pt(P(m-C6H4SO3Na)3)2Cl2 and its tin chloride analogue on a controlled-pore glass, Journal of Molecular Catalysis, 1991, 70, p. 363-368.

Toth, et al., "Immobilization of HRh(CO)(P(m-C6H4SO3Na)3)3 on an Anion Exchange Resin for the Hydroformylation of Higher Olefins", Catalysis Letters, 1991, 8, p. 209-214.

Guo, et al., "Bis[tris(m-(sodium sulfonato)phenyl)phosphine] hexacarbonyl dicobalt, Co2(CO)6(P(m-C6H4SO3Na)3)2, in a supported aqueous phase for the hydroformylation of 1-hexene" Journal of Organometallic Chememistry, 1991,203, p. 221-227.

Arhancet, et al., "Hydroformylation by supported aqueous-phase catalysis: a new class of heterogeneous catalysts" Nature, Jun. 8, 1989, 339, p. 454-455.

Rode, et al., "Propylene Hydroformylation on Rhodum Zeolites X and Y", Journal of Catalysis, 1985, 96, p. 563-573.

Davis, et al., "Hydroformylation of 1-hexene by soluble and zeolite-supported rhodium species Part II", Journal of Molecular Catalysis, 1987, 39, p. 243-259.

Feldman, et al., "Membrane-supported rhodium hydroformylation catalysts", Journal of Molecular Catalysis, 1990, 63, p. 213-221.

Jongsma, et al., "Fine tuning of bulky-phosphite modified rhodium catalysts by binding them to copolymers", Journal of Molecular Catalysis, 1993, 83, p. 17-35.

Lieto, et al., "Polymeric supports for catalysts", Chemtech, 13, No. 1, Jan. 1983, p. 46-53.

Parrinello, et al., "Asymmetric Hydroformylation Catalyzed by Homogeneous and Polymer-Supported Platinum Complexes Containing Chiral Phosphine Ligands", Jounal of American Chemical Society, 1987, 109, p. 7122-7127.

Jongsma, et al., "A new type of highly active polymer-bound rhodium hydroformylation catalyst", Polymer, 1992, 33, p. 161-165.

Bergbreiter, et al., "Polyethylene-Bound Soluble Recoverable Palladium(0) Catalysts", J. Org. Chem. 1989, 54, p. 2726-2730.

PCT/US2013/058714, International Search Report and Written Opinion with a mailing date of Oct. 29, 2013.

PCT/US2013/058714, International Preliminary Report on Patentability with a mailing date of Apr. 9, 2015.

HYDROFORMYLATION PROCESS

CROSS-REFERENCE TO RELATED APPLICATIONS

This application claims priority from provisional application Ser. No. 61/734,089, filed Dec. 6, 2012, which is incorporated herein by reference in its entirety.

BACKGROUND OF THE INVENTION

The invention relates to a hydroformylation process wherein CO, $H_2$ and at least one olefin are contacted under hydroformylation conditions sufficient to form at least one aldehyde product in the presence of a catalyst.

It is well known in the art that aldehydes can be produced by reacting an olefinically unsaturated compound with carbon monoxide and hydrogen in the presence of a rhodium-organophosphite ligand complex catalyst. The product of this hydroformylation reaction process may include certain aldehyde derivatives, depending upon the reaction process. Derivatives of aldehydes include alcohols, acids, and polyols. Such aldehydes have a wide range of utility and are useful, for example, as intermediates for hydrogenation to aliphatic alcohols, for aldol condensation to produce plasticizers, and for oxidation to produce aliphatic acids.

Preferred hydroformylation processes involve continuous hydroformylation and recycling of the catalyst solution such as disclosed, for example, in U.S. Pat. Nos. 4,148,830; 4,717,775 and 4,769,498. However, notwithstanding the benefits attendant with such liquid recycle hydroformylation processes, stabilization of the catalyst and organophosphite ligand remains a primary concern of the art. Catalyst stability is a key issue in the employment of any catalyst. Loss of catalyst or catalytic activity due to undesirable reactions of the highly expensive rhodium catalyst can be detrimental to the production of the desired aldehyde. Likewise, degradation of the organophosphite ligand employed during the hydroformylation process can lead to the formation of poisoning organophosphite compounds or inhibitors or acidic by-products that can lower the activity of the rhodium catalyst. Moreover, aldehyde production costs increase when catalyst productivity decreases.

Those skilled in the art recognize that hydrolytic instability of the organophosphite ligands is a major cause of organophosphite ligand degradation and catalyst deactivation in rhodium-organophosphite ligand complex catalyzed hydroformylation processes. All organophosphites are susceptible to hydrolysis to some degree, the rate of hydrolysis of organophosphites in general being dependent on the stereochemical nature of the organophosphite. In parallel, the analogous alcoholysis reaction wherein P—OR moieties are exchanged can also significantly alter the nature of the phosphites present in the system. In general, the bulkier the steric environment around the phosphorus atom, the slower the hydrolysis rate. Moreover, all such hydrolysis reactions invariably produce phosphorus acidic compounds that catalyze the hydrolysis reactions. For example, the hydrolysis of a tertiary organophosphite produces a phosphonic acid diester, which is hydrolyzable to a phosphonic acid monoester, which in turn is hydrolyzable to $H_3PO_3$, a strong acid. Moreover, hydrolysis of the ancillary products of side reactions, such as the reaction between a phosphonic acid diester and the aldehyde, or between certain organophosphite ligands and an aldehyde, can lead to the production of undesirable strong aldehyde acids, e.g., $n\text{-}C_3H_7CH(OH)P(O)(OH)_2$.

Even highly desirable sterically-hindered organobisphosphites that are not very hydrolyzable can react with the aldehyde product to form poisoning organophosphites, e.g., organomonophosphites, which are not only catalytic inhibitors, but are far more susceptible to hydrolysis and the formation of such aldehyde acid by-products, e.g., hydroxy alkyl phosphonic acids, as shown, for example, in U.S. Pat. Nos. 5,288,918 and 5,364,950. Further, the hydrolysis of organophosphite ligands may be considered as being autocatalytic in view of the production of phosphorus acidic compounds, e.g., $H_3PO_3$, aldehyde acids such as hydroxy alkyl phosphonic acids, $H_3PO_4$ and the like, and if left unchecked the catalyst system of the continuous liquid recycle hydroformylation process will become more and more acidic. Thus, in time the eventual build-up of an unacceptable amount of such phosphorus acidic materials can cause the total destruction of the organophosphite present, thereby rendering the hydroformylation catalyst totally ineffective (deactivated) and the valuable rhodium metal susceptible to loss, e.g., due to precipitation and/or deposition on the walls of the reactor.

U.S. Pat. No. 5,741,942 (col. 1) and U.S. Pat. No. 5,288,918 (col. 24) teach that one of the major problems with Rh-phosphite-based hydroformylation is the formation of alternative phosphites due to degradation of the original phosphite. The "poisoning phosphite" structure shown in '918 involves a less sterically-hindered phosphite which is capable of binding to an active Rh catalyst, rendering it inactive towards the desired hydroformylation reaction until such time that it decomposes further and the rhodium is liberated again. There are several known ways to produce this "poisoning phosphite," which include the rhodium-catalyzed reaction shown in '918 or simple alcoholysis of the phosphite (which can be acid- or base-catalyzed). Since the desirable phosphite ligands are sterically congested, these reactions tend to be slow under the conditions present in the hydroformylation reactors. The presence of significant amounts of any poisoning phosphite is undesired in that it lowers plant efficiency.

Numerous methods have been proposed to maintain catalyst and/or organophosphite ligand stability and thereby minimize poisoning phosphite formation. For instance, U.S. Pat. No. 5,288,918 suggests employing a catalytic activity enhancing additive, such as water and/or a weakly acidic compound. U.S. Pat. No. 5,364,950 suggests adding an epoxide to stabilize the organophosphite ligand. Other factors, such as control of acidity, are important to minimize the formation of the "poisoning phosphite" or to selectively decompose any that have formed. U.S. Pat. No. 5,741,944 teaches the use of an aqueous extractor with optional amine additives to remove at least a portion of the acids as they are formed, and U.S. Pat. No. 5,763,677 teaches the use of an ion exchange resin to remove acidic species. U.S. Pat. No. 4,774,361 suggests carrying out the vaporization separation employed to recover the aldehyde product from the catalyst in the presence of an organic polymer containing polar functional groups selected from the class consisting of amide, ketone, carbamate, urea, and carbonate radicals in order to prevent and/or lessen rhodium precipitation from solution.

It is also known that phosphites decompose in the presence of alcohols, especially primary alcohols such as methanol. US 2010/0267991 (col. 4+) discloses the issue of alcoholysis of phosphites and emphasizes the importance of steric bulk about the phosphorous to minimize the hydrolysis/alcoholysis reactions. U.S. Pat. No. 6,307,110 (col. 23, ln. 55) teaches to avoid using primary alcohols with phosphite-based hydroformylation reactions. Methanol is the most reactive primary alcohol due to the lack of steric hindrance. Methanol can react with phosphites to generate methoxy-phosphite derivates, which will be substantially less sterically congested and thus highly likely to be significant hydroformylation catalyst inhibitors. U.S. Pat. No. 3,527,809 teaches that going from phenoxy- to methoxy-based phosphites reduces the ΔHNP by over 300, reinforcing the negative impact of methoxy-based phosphites. The impact of steric congestion (or ligand cone angle) is also discussed in U.S. Pat. No. 5,741,945 wherein it is taught that non-bulky monophosphite ligands cannot be used since they compete with CO, which interferes with the hydroformylation reaction.

Notwithstanding the value of the teachings of said references, the search for alternative methods and hopefully an even better and more efficient means for stabilizing the rhodium catalyst and organophosphite ligand employed remains an ongoing activity in the art. Recent advances in coal-to-chemicals technology has presented a new challenge for hydroformylation technology. Olefins that are used to produce aldehyde products traditionally have been made by cracking petroleum feedstocks, i.e., producing low molecular weight hydrocarbons from high molecular weight hydrocarbons. A new alternative source of olefins is by oxygenate conversion processes in an oxygenate-to-olefins unit (e.g., a methanol-to-olefins unit of U.S. Pat. No. 5,914,433). Methanol is used in the commercial scale preparation of olefins, such as in methanol-to-olefins processes described above as well as in purification schemes such as isobutylene removal from raffinate streams (generating MTBE, an additive used in gasoline or to regenerate isobutylene for polyisobutylene). Residual methanol from traditional hydrocarbon-based sources been kept at very low levels, e.g., <100 ppm but the newer sources of olefins may have substantially higher levels than found in traditional sources.

Industrial olefin feeds contain impurities such as sulphur, and the removal of undesirable by-products from an olefin stream can be quite difficult. For example, the removal of sulfur, nitrogen and chlorine or the removal of dimethyl ether (DME) from $C_4$ or $C_5$ raffinate recovered from a methyl tertiary butyl ether (MTBE) or a tertiary amyl methyl ether (TAME) unit; or the removal of oxygenate by-products, including dimethyl ether, from an oxygenate-to-olefins unit can require a significant amount of olefin feed pretreatment.

Syngas is a widely used industrial gas that comprises CO and $H_2$. Coal is converted to syngas in plants using coal-to-chemicals technologies. The syngas is converted to other chemicals such as methanol and a variety of olefins. The syngas and the olefins are used for other downstream processes and may contain various levels of methanol due to blow-back contamination or due to vent recycle from these other processes.

Feeds with high levels of methanol may generate catalyst solutions with substantially higher levels of methanol than observed before, thereby increasing the possibility of generating methanol-based, sterically unhindered alcoholysis products which may exhibit severe reaction inhibition.

The presence of alcohols during hydroformylation in the presence of phosphines is known. EP 420 510 reports the hydroformylation of olefins in the presence of alcohols and phosphine ligands. However, phosphines are different from phosphites, in that they do not undergo hydrolysis/alcoholysis reactions. U.S. Pat. No. 4,148,830 teaches that aldehyde condensation adducts can be used as a solvent for phosphine and phosphite-based rhodium hydroformylation in long-term, continuous operation. These condensation adducts are bulky alcohols, ethers, or esters.

Diebolt et al., *Advanced Synthesis & Catalysis*, 354, Issue 4, March 2012, pp. 670-677, and Ali et al., *J. Mol. Cat. A*, 2005, 230, 9, showed that phosphites could be used in the presence of methanol in a batch-mode operation but generated acetals rather than the aldehyde. The stability of the ligands is not discussed and, in fact, the process worked well in the absence of any phosphorous ligand.

WO 2005/093010 discloses the hydroformylation of propylene containing up to 10% oxygenate contaminates including methanol (among others) using a wide variety of catalysts. No catalyst stability or long-term continuous operation data is presented.

Since ligand hydrolysis is always a concern, balancing hydrolysis vs alcoholysis rates of phosphite ligands has not been reported in the presence of a highly reactive alcohol such as methanol. In addition, the relative rates of hydrolysis of the corresponding methoxy-based poisoning phosphites has not been reported. The reactions cited in '918 are based on butanol but there are no reports of similar reactions involving methanol and there is no information regarding the potential buildup of methoxy-based phosphite inhibitors nor any means to remove them. It would be, therefore, desirable to find olefin hydroformylation methods that do not require extensive pretreatment of the olefin feed to remove contaminants.

It also would be desirable to have a hydroformylation process that could tolerate feedstocks containing higher amounts of methanol. For example, it would be desirable to have a hydroformylation process that could use olefins and/or syngas from coal-to-chemicals plants, e.g. feed streams contaminated with methanol, as this would avoid the need for extensive processing to remove residual methanol from the feed components, which removal requires additional capital expense and processing costs.

SUMMARY OF THE INVENTION

The process of the invention is such a hydroformylation process comprising:

(a) contacting in a reaction zone reactants comprising an olefin, hydrogen and CO in the presence of a metal hydrolyzable phosphorous ligand complex catalyst and, optionally, free hydrolyzable phosphorous ligand, under reaction conditions sufficient to produce an aldehyde product in a reaction fluid, with the proviso that at least one of the reactants comprises methanol and that the total amount of methanol in the reactants, prior to entering the reaction zone, is from 200 ppm to 10 percent of the total weight of methanol and the reactants, (b) removing at least a portion of the reaction fluid from the reaction zone to a separation zone, and separating the reaction fluid in the separation zone to produce a hydroformylation reaction product stream and a catalyst recycle stream, (c) treating at least a portion of said catalyst recycle stream with an aqueous buffer solution under conditions sufficient to neutralize and remove at least some amount of one or more phosphorus acidic compounds from said product stream.

Surprisingly, the catalyst does not substantially deactivate even in the presence of these high amounts of methanol.

DETAILED DESCRIPTION OF THE INVENTION

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and non-aromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and non-aromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

"Hydrolyzable phosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, and fluorophosphites. The ligands may include chelate structures and/or may contain multiple P—Z moieties such as polyphosphites, polyphosphoramidites, etc. and mixed P—Z moieties such as phosphite-phosphoramidites, and flurophosphite-phosphites.

The term "complex" as used herein means a coordination compound formed by the union of one or more electronically rich molecules or atoms (i.e., ligand) with one or more electronically poor molecules or atoms (i.e., transition metal). For example, the organophosphorous ligand employable herein possesses at least one phosphorus (III) donor atom having one unshared pair of electrons, which is capable of forming a coordinate bond with the metal.

The disclosed process comprises contacting reactants comprising CO, $H_2$ and at least one olefin under hydroformylation conditions sufficient to form at least one aldehyde product in the presence of a catalyst comprising, as components, a transition metal and a hydrolyzable phosphorous ligand. Optional process components include an amine and/or water.

In one embodiment of the invention, the invention is concerned with a method comprising hydroformylating a stream that is rich in olefins that have been obtained from the product produced in the conversion of oxygenates-to-olefins or from other sources wherein a prior processing step is used to remove some components (e.g., isobutylene). According to the process of the invention, the olefin-containing stream may be hydroformylated even if it contains a relatively high amount of methanol.

Methanol can be present in only one, or any combinations of the reactants. The amount of methanol can be from 200 ppm to 10 percent, based on the total weight of olefin, CO, hydrogen and methanol. In various embodiments of the invention, the amount of methanol is at least 400 ppm, at least 1,000 ppm or at least 1 percent.

Hydrogen and carbon monoxide are required for the process. These may be obtained from any suitable source, including petroleum cracking and refinery operations. Syngas mixtures are preferred as a source of hydrogen and CO.

Syngas (from synthesis gas) is the name given to a gas mixture that contains varying amounts of CO and $H_2$. Production methods are well known and include, for example: (1) steam reforming and partial oxidation of natural gas or liquid hydrocarbons; and (2) the gasification of coal and/or biomass. Hydrogen and CO typically are the main components of syngas, but syngas may contain carbon dioxide and inert gases such as $N_2$ and Ar. The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications. For the purposes of this invention, the syngas may contain amounts of methanol that were heretofore considered to be unacceptable. The amount of methanol may be constant or variable depending on upstream plant variability.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 3 to 20, carbon atoms. These compounds are described in detail in US 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

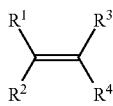

wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene.

Illustrative optically active or prochiral olefinic compounds useful in asymmetric hydroformylation are described, for example, in U.S. Pat. Nos. 4,329,507, 5,360,938 and 5,491,266.

The olefins employed in the invention may have residual methanol either from the olefin manufacture or purification or impurity removal processes. In coal-to-chemicals processes wherein coal is converted to syngas then to methanol which itself is converted to higher molecular weight chemicals such as olefins, separation and recycling of the methanol may not be entirely complete and residual methanol may remain in the olefin(s). In raffinate streams, removal of isobutene by conversion to MTBE (methyl-t-butyl ether) by reaction of isobutene with methanol may also leave residual methanol in the resulting butene stream. Inefficient distillation or process interruptions may result in olefins with elevated methanol levels.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g. acetone and methylethyl ketone), esters (e.g. ethyl acetate, di-2-ethylhexyl phthalate, 2,2,4-trimethyl-1,3-pentanediol monoisobutyrate), hydrocarbons (e.g. toluene), nitrohydrocarbons (e.g. nitrobenzene), ethers (e.g. tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands.

Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are monoorganophosphite, diorganophosphite, triorganophosphite and organopolyphosphite compounds. Such organophosphorous ligands and methods for their preparation are well known in the art.

Representative monoorganophosphites may include those having the formula:

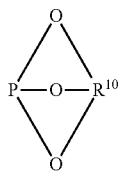
<<I>> wherein $R^{10}$ represents a substituted or unsubstituted trivalent hydrocarbon radical containing from 4 to 40 carbon atoms or greater, such as trivalent acyclic and trivalent cyclic radicals, e.g., trivalent alkylene radicals such as those derived from 1,2,2-trimethylolpropane, or trivalent cycloalkylene radicals such as those derived from 1,3,5-trihydroxycyclohexane. Such monoorganophosphites may be found described in greater detail, for example, in U.S. Pat. No. 4,567,306.

Representative diorganophosphites may include those having the formula:

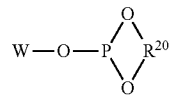
<<II>> wherein $R^{20}$ represents a substituted or unsubstituted divalent hydrocarbon radical containing from 4 to 40 carbon atoms or greater and W represents a substituted or unsubstituted monovalent hydrocarbon radical containing from 1 to 18 carbon atoms or greater.

Representative substituted and unsubstituted monovalent hydrocarbon radicals represented by W in the above Formula (II) include alkyl and aryl radicals, while representative substituted and unsubstituted divalent hydrocarbon radicals represented by $R^{20}$ include divalent acyclic radicals and divalent aromatic radicals. Illustrative divalent acyclic radicals include, for example, alkylene, alkylene-oxy-alkylene, alkylene-S-alkylene, cycloalkylene radicals, and, alkylene-NR$^{24}$-alkylene wherein $R^{24}$ is hydrogen or a substituted or unsubstituted monovalent hydrocarbon radical, e.g., an alkyl radical having 1 to 4 carbon atoms. The more preferred divalent acyclic radicals are the divalent alkylene radicals such as disclosed more fully, for example, in U.S. Pat. Nos. 3,415,906 and 4,567,302. Illustrative divalent aromatic radicals include, for example, arylene, bisarylene, arylene-alkylene, arylene-alkylene-arylene, arylene-oxy-arylene, arylene-NR$^{24}$-arylene wherein $R^{24}$ is as defined above, arylene-S-arylene, and arylene-S-alkylene. More preferably $R^{20}$ is a divalent aromatic radical such as disclosed more fully, for example, in U.S. Pat. Nos. 4,599,206, 4,717,775, and 4,835,299.

Representative of a more preferred class of diorganophosphites are those of the formula:

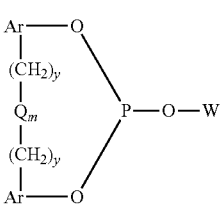
<<III>> wherein W is as defined above, each Ar is the same or different and represents a substituted or unsubstituted aryl radical, each y is the same or different and is a value of 0 or 1, Q represents a divalent bridging group selected from —C(R$^{33}$)$_2$—, —O—, —S—, —NR$^{24}$—, Si(R$^{35}$)$_2$ and —CO—, wherein each $R^{33}$ is the same or different and represents hydrogen, an alkyl radical having from 1 to 12 carbon atoms, phenyl, tolyl, and anisyl, $R^{24}$ is as defined above, each $R^{35}$ is the same or different and represents hydrogen or a methyl radical, and m has a value of 0 or 1. Such diorganophosphites are described in greater detail, for example, in U.S. Pat. Nos. 4,599,206, 4,717,775, and 4,835,299.

Representative triorganophosphites may include those having the formula:

<<IV>> wherein each $R^{46}$ is the same or different and is a substituted or unsubstituted monovalent hydrocarbon radical e.g., an alkyl, cycloalkyl, aryl, alkaryl and aralkyl radicals that may contain from 1 to 24 carbon atoms. Illustrative triorganophosphites include, for example, trialkyl phosphites, dialkylaryl phosphites, alkyldiaryl phosphites, triaryl phosphites, such as, for example, trimethyl phosphite, triethyl phosphite, butyldiethyl phosphite, dimethylphenyl phosphite, triphenyl phosphite, trinaphthyl phosphite, bis(3,6,8-tri-t-butyl-2-naphthyl)methylphosphite, bis(3,6,8-tri-t-butyl-2-naphthyl)cyclohexylphosphite, tris(3,6-di-t-butyl-2-naphthyl)phosphite, bis(3,6,8-tri-t-butyl-2-naphthyl) phenylphosphite, and bis(3,6,8-tri-t-butyl-2-naphthyl)(4-sulfonylphenyl)phosphite. The most preferred triorganophosphite is triphenylphosphite. Such triorganophosphites are described in greater detail, for example, in U.S. Pat. Nos. 3,527,809 and 5,277,532.

Representative organopolyphosphites contain two or more tertiary (trivalent) phosphorus atoms and may include those having the formula:

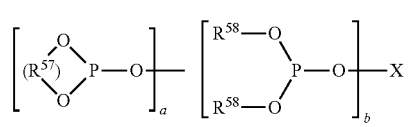
<<V>> wherein X represents a substituted or unsubstituted n-valent organic bridging radical containing from 2 to 40 carbon atoms, each $R^{57}$ is the same or different and represents a divalent organic radical containing from 4 to 40 carbon atoms, each $R^{58}$ is the same or different and represents a substituted or unsubstituted monovalent hydrocarbon radical containing from 1 to 24 carbon atoms, a and b can be the same or different and each have a value of 0 to 6, with the proviso that the sum of a+b is 2 to 6 and n equals a+b. It is to be understood that when a has a value of 2 or more, each $R^{57}$ radical may be the same or different. Each $R^{58}$ radical may also be the same or different in any given compound.

Representative n-valent (preferably divalent) organic bridging radicals represented by X and representative divalent organic radicals represented by $R^{57}$ above, include both acyclic radicals and aromatic radicals, such as alkylene, alkylene-$Q_B$-alkylene, cycloalkylene, arylene, bisarylene, arylene-alkylene, and arylene-$(CH_2)_y$-$Q_m$-$(CH_2)_y$-arylene radicals, wherein each Q, y and m are as defined above in Formula (III). The more preferred acyclic radicals represented by X and $R^{57}$ above are divalent alkylene radicals, while the more preferred aromatic radicals represented by X and $R^{57}$ above are divalent arylene and bisarylene radicals, such as disclosed more fully, for example, in U.S. Pat. Nos. 4,769,498; 4,774,361: 4,885,401; 5,179,055; 5,113,022; 5,202,297; 5,235,113; 5,264,616 and 5,364,950, and 5,527,950. Representative preferred monovalent hydrocarbon radicals represented by each $R^{58}$ radical above include alkyl and aromatic radicals.

Illustrative preferred organopolyphosphites may include bisphosphites such as those of Formulas (VI) to (VIII) below:

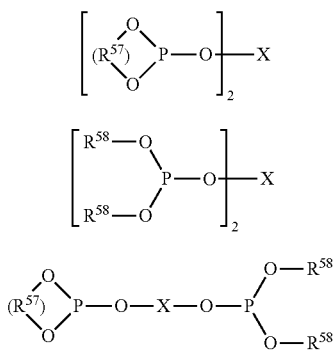

wherein each $R^{57}$, $R^{58}$ and X of Formulas (VI) to (VIII) are the same as defined above for Formula (V). Preferably each $R^{57}$ and X represents a divalent hydrocarbon radical selected from alkylene, arylene, arylene-alkylene-arylene, and bisarylene, while each $R^{58}$ radical represents a monovalent hydrocarbon radical selected from alkyl and aryl radicals. Organophosphite ligands of such Formulas (V) to (VIII) may be found disclosed, for example, in U.S. Pat. Nos. 4,668,651; 4,748,261; 4,769,498; 4,774,361; 4,885,401; 5,113,022; 5,179,055; 5,202,297; 5,235,113; 5,254,741; 5,264,616; 5,312,996; 5,364,950; and 5,391,801.

$R^{10}$, $R^{20}$, $R^{46}$, $R^{57}$, $R^{58}$, Ar, Q, X, m, and y in Formulas (VI) to (VIII) are as defined above. Most preferably X represents a divalent aryl-$(CH_2)_y$-$(Q)_m$-$(CH_2)_y$-aryl radical wherein each y individually has a value of 0 or 1; m has a value of 0 or 1 and Q is —O—, —S— or —$C(R^{35})_2$— where each $R^{35}$ is the same or different and represents hydrogen or a methyl radical.

More preferably each alkyl radical of the above defined $R^8$ groups may contain from 1 to 24 carbon atoms and each aryl radical of the above-defined Ar, X, $R^{57}$ and $R^{58}$ groups of the above Formulas (VI) to (VII) may contain from 6 to 18 carbon atoms and said radicals may be the same or different, while the preferred alkylene radicals of X may contain from 2 to 18 carbon atoms and the preferred alkylene radicals of $R^{57}$ may contain from 5 to 18 carbon atoms. In addition, preferably the divalent Ar radicals and divalent aryl radicals of X of the above formulas are phenylene radicals in which the bridging group represented by —$(CH_2)_y$-$(Q)_m$-$(CH_2)_y$— is bonded to said phenylene radicals in positions that are ortho to the oxygen atoms of the formulas that connect the phenylene radicals to their phosphorus atom of the formulae. It is also preferred that any substituent radical when present on such phenylene radicals be bonded in the para and/or ortho position of the phenylene radicals in relation to the oxygen atom that bonds the given substituted phenylene radical to its phosphorus atom.

Any of the $R^{10}$, $R^{20}$, $R^{57}$, $R^{58}$, W, X, Q and Ar radicals of such organophosphites of Formulas (I) to (VIII) above may be substituted if desired, with any suitable substituent containing from 1 to 30 carbon atoms that does not unduly adversely affect the desired result of the process of this invention. Substituents that may be on said radicals in addition to corresponding hydrocarbon radicals such as alkyl, aryl, aralkyl, alkaryl and cyclohexyl substituents, may include for example silyl radicals such as —$Si(R^{35})_3$; amino radicals such as —$N(R^{15})_2$; phosphine radicals such as -aryl-$P(R^{15})_2$; acyl radicals such as —$C(O)R^{15}$ acyloxy radicals such as —OC$(O)R^{15}$; amido radicals such as —$CON(R^{15})_2$ and —$N(R^{15})COR^{15}$; sulfonyl radicals such as —$SO_2R^{15}$, alkoxy radicals such as —$OR^{15}$; sulfinyl radicals such as —$SOR^{15}$, phosphonyl radicals such as —$P(O)(R^{15})_2$, as well as halo, nitro, cyano, trifluoromethyl, and hydroxy radicals, wherein each $R^{15}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —$N(R^{15})_2$ each $R^{15}$ taken together can also represent a divalent bridging group that forms a heterocyclic radical with the nitrogen atom, and in amido substituents such as —C(O)N$(R^{15})_2$ and —$N(R^{15})COR^{15}$ each $R^{15}$ bonded to N can also be hydrogen. It is to be understood that any of the substituted or unsubstituted hydrocarbon radicals groups that make up a particular given organophosphite may be the same or different.

More specifically illustrative substituents include primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and octadecyl; aryl radicals such as phenyl, and naphthyl; aralkyl radicals such as benzyl, phenylethyl and triphenylmethyl; alkaryl radicals such as tolyl, and xylyl; alicyclic radicals such as cyclopentyl, cyclohexyl, 1-methylcyclohexyl, cyclooctyl, and cyclohexylethyl; alkoxy radicals such as methoxy, ethoxy, propoxy, t-butoxy, —$OCH_2CH_2OCH_3$, —$O(CH_2CH_2)_2OCH_3$, and —$O(CH_2CH_2)_3OCH_3$; aryloxy radicals such as phenoxy; as well as silyl radicals such as —$Si(CH_3)_3$, —$Si(OCH_3)_3$, and —$Si(C_3H_7)_3$; amino radicals such as —$NH_2$, —$N(CH_3)_2$, —$NHCH_3$, and —$NH(C_2H_5)$; arylphosphine radicals such as —$P(C_6H_5)_2$; acyl radicals such as —$C(O)CH_3$, —$C(O)C_2H_5$, and —$C(O)C_6H_5$; carbonyloxy radicals such as —C(O)OCH; oxycarbonyl radicals such as —$O(CO)C_6H_5$; amido radicals such as —$CONH_2$, —$CON(CH_3)_2$, and —$NHC(O)CH_3$; sulfonyl radicals such as —$S(O)_2C_2H_5$; sulfinyl radicals such as —$S(O)CH_3$; sulfidyl radicals such as —SCH$_3$, —C$_2$H$_5$, and —SC$_6$H$_5$; phosphonyl radicals such as —P(O)(C$_6$H$_5$)$_2$, —P(O)(CH$_3$)$_2$, —P(O)(C$_2$H$_5$)$_2$, —P(O)(C$_3$H$_7$)$_2$, —P(O)(C$_4$H$_9$)$_2$, —P(O)(C$_6$H$_{13}$)$_2$, —P(O)CH$_3$(C$_6$H$_5$), and —P(O)(H)(C$_6$H$_5$).

Specific illustrative examples of such organophosphite ligands include the following: 2-t-butyl-4-methoxyphenyl(3,3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis[2-(1,1-dimethylethyl)-4-methoxyphenyl]ester of phosphorous acid.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, Rh$_2$O$_3$, Rh$_4$(CO)$_{12}$, Rh$_6$(CO)$_{16}$, and Rh(NO$_3$)$_3$ may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphite ligand complex precursor, a solvent and, optionally, free organophosphite ligand. The preferred catalyst precursor composition can be prepared by forming a solution of rhodium dicarbonyl acetylacetonate, an organic solvent and a organophosphite ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 50 moles of organophosphorous ligand per mole of metal present in the reaction medium. More preferably, for organopolyphosphites, from 1.1 to 4 moles of organopolyphosphite ligand are employed per mole of metal. Said amounts of organophosphorous ligand are the sum of both the amount of organophosphorous ligand that is bound (complexed) to the metal present and the amount of free organophosphorous ligand present. If desired, additional organophosphorous ligand can be supplied to the reaction medium of the hydroformylation process at any time and in any suitable manner, e.g., to maintain a predetermined level of free ligand in the reaction medium.

In one embodiment, the rhodium catalyst may be impregnated onto any solid support, such as inorganic oxides, (i.e., alumina, silica, titania, or zirconia) carbon, or ion exchange resins, supported on, or intercalated inside the pores of, a zeolite, glass or clay, or may also be dissolved in a liquid film coating the pores of said zeolite or glass. Such zeolite-supported catalysts are particularly advantageous for producing one or more regioisomeric aldehydes in high selectivity, as determined by the pore size of the zeolite. The solid catalyst thus formed may still be complexed with one or more of the ligands defined above. Descriptions of such solid catalysts may be found in for example: *J. Mol. Cat.* 1991, 70, 363-368; *Catal. Lett.* 1991, 8, 209-214; *J. Organomet. Chem,* 1991, 403, 221-227; *Nature,* 1989, 339, 454-455; *J. Catal.* 1985, 96, 563-573; *J. Mol. Cat.* 1987, 39, 243-259. The catalyst may be attached to a thin film or membrane support, such as cellulose acetate or polyphenylenesulfone, as described in, for example, *J. Mol. Cat.,* 1990, 63, 213-221. The catalyst may be attached to an insoluble polymeric support through an organophosphorus-containing ligand, such as a phosphite, incorporated into the polymer. Descriptions of polymer-supported catalysts may be found in for example: *J. Mol. Cat.,* 1993, 83, 17-35; *Chemtech* 1983, 46; *J. Am. Chem. Soc.,* 1987, 109, 7122-7127. In another embodiment, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer,* 1992, 33, 161; *J. Org. Chem.* 1989, 54, 2726-2730.

The use of an aqueous buffer solution, such as in an extraction system, to prevent and/or lessen hydrolytic degradation of an organophosphite ligand and deactivation of a metal-organophosphite ligand complex is well-known and is disclosed, e.g., in U.S. Pat. No. 5,741,942 and U.S. Pat. No. 5,741,944. Such buffer systems and/or methods for their preparation are well known in the art and include oxyacid salts such phosphate and carboxylate salts (e.g., citrate, maleate, furate). Mixtures of buffers may be employed.

Illustrative metal-organophosphorous ligand complex catalyzed hydroformylation processes that may experience hydrolytic degradation include those processes as described, for example, in U.S. Pat. Nos. 4,148,830; 4,593,127; 4,769,498; 4,717,775; 4,774,361; 4,885,401; 5,264,616; 5,288,918; 5,360,938; 5,364,950; 5,491,266 and 7,196,230. Species containing the P—Z moiety that will likely undergo hydrolytic degradation include organophosphonites, phosphoramidites, and fluorophosphonites such as described WO 2008/071508, WO 2005/042458, and U.S. Pat. Nos. 5,710,344, 6,265,620, 6,440,891, 7,009,068, 7,145,042, 7,586,010, 7,674,937, and 7,872,156. These species will generate a variety of acidic and/or polar degradation products that can be extracted by use of the extractor technology taught in U.S. Pat. Nos. 5,744,649 and 5,741,944. Accordingly, the hydroformylation processing techniques that are advantageously employed may correspond to any known processing techniques such as, for example, gas recycle, liquid recycle, and combinations thereof. Preferred hydroformylation processes are those involving catalyst liquid recycle.

Extraction contacting conditions may vary greatly and any suitable combination of such conditions may be employed herein. For instance, a decrease in one of such conditions may be compensated for by an increase in one or more of the other conditions, while the corollary is also true. In general, liquid temperatures ranging from 10° C. to 120° C., preferably from 20° C. to 80° C., and more preferably from 25° C. to 60° C., should be suitable for most instances, although lower or higher temperatures may be employed if desired. Advantageously, the treatment is carried out at pressures ranging from ambient to reaction pressure, and the contact time may vary from a matter of seconds or minutes to a few hours or more.

Success in removing phosphorus acidic compounds from the reaction fluid may be determined by measuring the rate of degradation (consumption) of the organophosphorous ligand present in the hydroformylation reaction medium. The consumption rate can vary over a wide range, e.g., from <0.6 up to 5 grams per liter per day, and will be governed by the best compromise between cost of ligand and treatment frequency to keep hydrolysis below autocatalytic levels. Preferably, the aqueous buffer solution treatment is carried out in such a manner that the consumption of the desired organophosphorous ligand present in the hydroformylation reaction medium is maintained at an acceptable rate, e.g., <0.5 grams of ligand per liter per day, and more preferably <0.1 grams of ligand per liter per day, and most preferably <0.06 grams of ligand per liter per day. As the neutralization and extraction of phosphorus acidic compounds into the aqueous buffer solution proceeds, the pH of the buffer solution will slowly decrease.

The removal of at least some amount of phosphorus acidic compounds, for example, $H_3PO_3$, $H_3PO_4$, aldehyde acids such as hydroxy alkyl phosphonic acids, such as hydroxyl butyl phosphonic acid and hydroxyl pentyl phosphonic acid, from the hydroformylation system allows one to control the acidity of the hydroformylation reaction medium, thereby stabilizing the useful organophosphorous ligand by preventing or lessening its hydrolytic decomposition.

Optionally, an organic nitrogen compound may be added to the hydroformylation reaction fluid to scavenge the acidic hydrolysis by-products formed upon hydrolysis of the organophosphorous ligand, as taught, for example, in U.S. Pat. No. 4,567,306. Such organic nitrogen compounds may be used to react with and to neutralize the acidic compounds by forming conversion product salts therewith, thereby preventing the catalytic metal from complexing with the acidic hydrolysis by-products and thus helping to protect the activity of the catalyst while it is present in the reaction zone under reaction conditions.

Preferred organic nitrogen compounds useful for scavenging the phosphorus acidic compounds are heterocyclic compounds selected from the group consisting of diazoles, triazoles, diazines and triazines, such as those disclosed in U.S. Pat. No. 5,731,472. Benzimidazole and benztriazole are preferred. The amount of organic nitrogen compound that may be present in the reaction fluid is typically sufficient to provide a concentration of at least 0.0001 moles of free organic nitrogen compound per liter of reaction fluid. In general, the ratio of organic nitrogen compound to total organophosphorous ligand (whether bound or present as free organophosphorous ligand) is at least 0.1:1 and even more preferably at least 0.5:1. Organic nitrogen compound: organophosphorous ligand molar ratios of from 1:1 to 5:1 should be sufficient for most purposes.

The aqueous buffer solution treatment will not only remove free phosphoric acidic compounds from the metal-organophosphorous ligand complex catalyst containing reaction fluids, but it also removes the phosphorus acidic material of the conversion product salt formed by the use of the organic nitrogen compound scavenger when employed, i.e., the phosphorus acid of said conversion product salt remains behind in the aqueous buffer solution, while the treated reaction fluid, along with the reactivated (free) organic nitrogen compound is returned to the reaction zone.

The hydroformylation process, and conditions for its operation, are well known. The hydroformylation process may be asymmetric or non-asymmetric, the preferred process being non-asymmetric, and may be conducted in any batch, continuous or semi-continuous fashion and may involve any catalyst liquid and/or gas recycle operation desired. Thus, it should be clear that the particular hydroformylation process for producing such aldehydes from an olefinic unsaturated compound, as well as the reaction conditions and ingredients of the hydroformylation process are not critical features of this invention.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. No. 5,430,194 and U.S. Pat. No. 5,681,473, or by the more conventional and preferred method of distilling it, i.e. vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction fluid includes any fluid derived from any corresponding hydroformylation process that contains at least some amount of four different main ingredients or components, i.e., the aldehyde product, a metal-organophosphorous ligand complex catalyst, free organophosphorous ligand and a solvent for said catalyst and said free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed.

The reaction conditions of the hydroformylation process may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from −25° C. to 200° C., preferably from 50° C. to 120° C.

The hydroformylation process may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. The reaction zone employed may be a single vessel or may comprise two or more discrete vessels. The separation zone employed may be a single vessel or may comprise two or more discrete vessels. The buffer treatment zone employed in this invention may be a single vessel or may comprise two or more discreet vessels. The reaction zone(s) and separation zone(s) employed herein may exist in the same vessel or in different vessels. For example, reactive separation techniques such as reactive distillation, and reactive membrane separation may occur in the reaction zone(s).

The hydroformylation process can be conducted with recycle of unconsumed starting materials if desired. The reaction can be conducted in a single reaction zone or in a plurality of reaction zones, and in series or in parallel. The reaction steps may be effected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation process may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation process of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation process useful in this invention may be carried out in a multistaged reactor such as described, for example, in U.S. Pat. No. 5,728,893. Such multistaged reactors can be designed with internal, physical barriers that create more than one theoretical reactive stage per vessel.

It is generally preferred to carry out the hydroformylation process in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorous complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation, which is described, for example in U.S. Pat. Nos. 5,430,194 and 5,681,473.

As indicated above, desired aldehydes may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorous ligand and reaction products.

More particularly, distillation and separation of the desired aldehyde product from the metal-organophosphorous complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g., $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g., vaporizer/separator, wherein the desired aldehyde product is distilled. In general, distillation pressures ranging from vacuum pressures on up to total gas pressure of 340 kPa should be sufficient for most purposes.

Alternatively, in batch mode operation, the steps highlighted above may be separated by time rather than equipment. Some or all of the steps may be done in the same equipment but separated by time (i.e., performed in sequence). For heavier olefins, it may be preferable to charge the reactants into a batch reactor, perform the hydroformylation reaction by adding syngas until the reaction is completed, then perform the buffer treatment in the reactor (decanting the aqueous layer off) before (or after) product-catalyst separation (which itself may be a decant process as described in U.S. Pat. No. 5,932,772).

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, and 2-methyl-1-triacontanal.

Illustrative optically active aldehyde products include (enantiomeric) aldehyde compounds prepared by the asymmetric hydroformylation process of this invention such as, e.g. S-2-(p-isobutylphenyl)-propionaldehyde, S-2-(6-methoxy-2-naphthyl)propionaldehyde, S-2-(3-benzoylphenyl)-propionaldehyde, S-2-(3-fluoro-4-phenyl)phenylpropionaldehyde, and S-2-(2-methylacetaldehyde)-5-benzoylthiophene.

SPECIFIC EMBODIMENTS OF THE INVENTION

General Procedure

A liquid recycle reactor system is employed that consists of three 1 liter stainless steel stirred tank reactors connected in series. Each reactor is equipped with a vertically mounted agitator and a circular tubular sparger located near the bottom of the reactor. Each sparger contains a plurality of holes of sufficient size to provide the desired gas flow into the liquid body in the reactor. The spargers are used for feeding the olefin and/or syngas to the reactor, and can also be used to recycle unreacted gases to each reactor. Each reactor has a silicone oil shell as a means of controlling reactor temperature. Reactors 1 to 2 and reactors 2 to 3 are further connected via lines to transfer any unreacted gases and lines to allow a portion of the liquid solution containing aldehyde product and catalyst to be pumped from reactor 1 to reactor 2 and from reactor 2 to reactor 3. Hence, the unreacted olefin of reactor 1 is further hydroformylated in reactor 2 and subsequently reactor 3. Each reactor also contains a pneumatic liquid level controller for maintaining the desired liquid level. Reactor 3 has a blow-off vent for removal of unreacted gases.

A portion of the liquid reaction solution is continuously pumped from Reactor 3 to a vaporizer, which consists of a heated vessel at reduced pressure. The effluent stream from the vaporizer is sent to a gas-liquid separator located at the bottom of the vaporizer, where vaporized aldehyde is separated from the non-volatile components of the liquid reaction solution. The vaporized aldehyde product is condensed and collected in a product receiver. A pneumatic liquid level controller controls the desired non-volatile component level, including catalyst to be recycled, at the bottom of the separator. The separator is connected to the buffer treatment vessel by a recycle line.

The non-volatile components, including catalyst to be recycled, from the separator are passed into the bottom of an aqueous buffer treatment zone, or extractor, which consists of a phase separation zone and a packed column contacting region. The aqueous buffer, which is 0.4 molar sodium phosphate, is maintained at a specified pH of 6.5-7.2. Following the buffer treatment, the organic layer, which contains catalyst to be recycled, is pumped from the phase separation zone through a recycle line into Reactor 1.

Comparative Experiment A (Not an Embodiment of the Invention)

The process of the General Procedure is employed, and propylene is hydroformylated for 75 days.

The hydroformylation reaction is conducted by charging 3 liters of catalyst precursor comprising rhodium dicarbonyl acetylacetonate (about 75 ppm rhodium), about 0.25 wt % 6,6'-[[3,3',5,5'-tetrakis(1,1-dimethylethyl)-[1,1'-biphenyl]-2,2'-diyl]bis(oxy)]bisdibenzo[d,f][1,3,2]dioxaphosphepin ligand, which is a typical Formula VI ligand, (about 4 mole equivalents of ligand per mole equivalent of rhodium), and, as a solvent, about 15% tetraethylene glycol dimethyl ether and about 85 wt % $C_4$ aldehyde (n-butyraldehyde and iso-butyraldehyde in the ratio of about 30:1). The reactors are then heated to a reaction temperature of 70° C. under flowing carbon monoxide and hydrogen. Reactor 1, 2 and 3 pressures are maintained at 130, 110, and 90 psig respectively. Propylene is fed to reactor one at a rate of 1.8 gram moles per liter of reactor volume per hour. The above mentioned reaction conditions are maintained throughout the hydroformylation. The crude aldehyde product is separated with the vaporizer system operated at 8 psig and 98° C. During the run, catalyst performance is determined by process measurements and sample analysis by gas chromatography (GC). The formation of ligand degradation products throughout the run is tracked by high performance liquid chromatography (HPLC), ion chromatography (IC) and $^{31}$P NMR spectroscopy Example 1

The process of Comparative Experiment A is repeated except that methanol is added in various concentrations as described below.

Pure, HPLC grade methanol is degassed until oxygen free and pumped into the liquid recycle line prior to entering reactor 1. The methanol is fed at a rate sufficient to provide methanol contamination equivalent to about 580 ppmw and 5800 ppmw in the reactants. Hydroformylation with a methanol concentration consistent with a reactant contamination of 580 ppm methanol is performed for 47 days. For the remaining 28 days of the hydroformylation, 5800 ppmw methanol, as based on the weight of the reactants, is pumped to reactor 1.

When compared to the Comparative Experiment, no difference is detected in hydroformylation rate or selectivity to normal- and iso-butyraldehyde. When compared to the Comparative Experiment, no difference is detected in formation rate of ligand degradation products. Furthermore, no new phosphorous-based chemical intermediates are detected using $^{31}$P NMR spectroscopy over the course of the hydroformylation with methanol present.

Surprisingly, over the course of the 75 days of hydroformylation, the methanol fed at the above mentioned conditions does not cause any observable adverse affects to the performance of the hydroformylation catalyst or ligand degradation rates. Without being bound by theory, it appears that the methoxy-based poisoning phosphite either doesn't form or is hydrolyzed at a faster rate than it is generated (or at least faster than the product-based poisoning phosphite). By using the extractor to control the pH, the rate of formation of methoxy-based poisoning phosphite is kept low and/or the rate of hydrolysis of methoxy-based poisoning phosphite is fast enough such that there is no impact on the overall hydroformylation rate or ligand degradation rate.

What is claimed is:

1. A hydroformylation process comprising:
   (a) contacting in a reaction zone reactants comprising an olefin, hydrogen and CO in the presence of a metal hydrolyzable phosphorous ligand complex catalyst and, optionally, free hydrolyzable phosphorous ligand, under reaction conditions sufficient to produce an aldehyde product in a reaction fluid, with the proviso that at least one of the reactants comprises methanol and that the total amount of methanol in the reactants, prior to entering the reaction zone, is from 200 ppm to 10 percent of the total weight of methanol and the reactants,
   (b) removing at least a portion of the reaction fluid from the reaction zone to a separation zone, and separating the reaction fluid in the separation zone to produce a hydroformylation reaction product stream and a catalyst recycle stream,
   (c) treating at least a portion of said catalyst recycle stream with an aqueous buffer solution under conditions sufficient to neutralize and remove at least some amount of one or more phosphorus acidic compounds from said product stream.

2. The process of claim 1 wherein the amount of methanol is at least 400 ppm.

3. The process of claim 1 wherein the amount of methanol is at least 1,000 ppm.

4. The process of claim 1 wherein the amount of methanol is at least 10,000 ppm.

5. The process of claim 1 wherein the ligand comprises at least one of a bisphosphite, a diorganophosphite or a triorganophosphite.

6. The process of claim 1 wherein the metal is rhodium.

7. The process of claim 1 wherein the pH of the buffer solution is from 6 to 9.

8. The process of claim 1 wherein the ligand is a bisphosphite.

9. The process of claim 1 wherein the ligand is a diorganophosphite.

10. The process of claim 1 wherein the ligand is a triorganophosphite.

11. The process of claim 1 wherein the aqueous buffer is a phosphate salt.

12. The process of claim 1 wherein the aqueous buffer is a carboxylate salt.

* * * * *